(12) United States Patent
Kenten et al.

(10) Patent No.: US 7,662,642 B2
(45) Date of Patent: Feb. 16, 2010

(54) METHOD FOR DETECTION OF SPECIFIC ANTIBODIES USING UBIQUITIN FUSION PROTEINS

(75) Inventors: John H. Kenten, Boyds, MD (US); Alfonso Tramontano, Rockville, MD (US); Aprile L. Pilon, Gaithersburg, MD (US); Gerald L. Lohnas, Catonsville, MD (US); Steven F. Roberts, Bethesda, MD (US)

(73) Assignee: Wellstat BioCatalysis, LLC, Gaithersburg, MD (US)

( * ) Notice: Subject to any disclaimer, the term of this patent is extended or adjusted under 35 U.S.C. 154(b) by 34 days.

(21) Appl. No.: 10/681,388

(22) Filed: Oct. 7, 2003

(65) Prior Publication Data

US 2004/0170643 A1    Sep. 2, 2004

Related U.S. Application Data

(62) Division of application No. 09/964,201, filed on Sep. 26, 2001, now Pat. No. 6,660,271, which is a division of application No. 09/026,276, filed on Feb. 19, 1998, now Pat. No. 6,319,503.

(51) Int. Cl.
  *G01N 33/567* (2006.01)
  *G01N 33/53* (2006.01)
  *A61K 39/00* (2006.01)

(52) U.S. Cl. .................... 436/503; 436/547; 424/192.1
(58) Field of Classification Search .................. None
  See application file for complete search history.

(56) References Cited

U.S. PATENT DOCUMENTS 5,262,322 A    11/1993    Liu et al.
5,459,051 A    10/1995    Mascarenhas

OTHER PUBLICATIONS

Vannier B, Loosfelt H, Meduri G, Pichon C, and Milgrom E. 1996. Biochemistry. vol. 35, p. 1358-1366.*
Loosfelt H, Pichon C, Jolivet A, Misrahi M, Caillou B, Jamous M, Vannier B, and Milgrom E. 1992. Proc. Natl. Acad. Sci. USA. vol. 89, p. 3765-3769.*
Ecker et al., J. of Biol. Chem. 264 No. 13: 7715 (1989).
Monia et al., J. of Biol. Chem. 264 No. 7: 4093 (1989).
Vannier et al., Biochemistry 35: 1358 (1996).
Barry et al., Nature 377: 632 (1995).
Loosfelt et al., Proc. Natl. Acad. Sci. USA 89: 3765 (1992).
Pilon et al., Biotechnol. Prog. 13: 374-379 (1997).
Dalum et al., Molecular Immun. 34: 1113-1120 (1997).

* cited by examiner

*Primary Examiner*—Robert Landsman
*Assistant Examiner*—Bruce D Hissong
(74) *Attorney, Agent, or Firm*—Kevin M. Farrell, Esq.; Pierce Atwood, LLP

(57) ABSTRACT

Disclosed are epitope-containing heat shock fusion proteins, DNA constructs encoding such fusion proteins, and methods of use. More specifically, disclosed are ubiquitin fusion proteins comprising ubiquitin fused to a plurality of identical or non-identical epitopes at specified locations.

4 Claims, No Drawings

METHOD FOR DETECTION OF SPECIFIC ANTIBODIES USING UBIQUITIN FUSION PROTEINS

This application is a divisional of application Ser. No. 09/964,201, filed Sep. 26, 2001, now U.S. Pat. No. 6,660,271, which is a divisional of application Ser. No. 09/026,276, filed Feb. 19, 1998, now U.S. Pat. No. 6,319,503.

GOVERNMENT SUPPORT

The present invention was made with Government Support under National Institute of Allergy and Infectious Diseases Extramural Grant No. 1 R43 AI39906-01 from the Department of Health and Human Services, Public Health Service. The Government retains certain rights in the invention.

BACKGROUND OF THE INVENTION

The construction of immunogenic peptides or peptide conjugates is an active and ongoing research pursuit. The goals include production of reagent antibodies for research, for example in neurobiology, and production of synthetic vaccines for human or veterinary application. Small synthetic peptides are poor antigens and typically require covalent association with macromolecular carriers and administration with adjuvant in order to elicit an immune response. Carriers also provide T-cell epitopes necessary for cell-mediated response and for helper functions in the humoral response. When presented appropriately, synthetic peptides can elicit antibodies against large proteins which display the same peptide epitope within their sequence. Vaccine research further seeks to define those synthetic immunogens capable of inducing an antibody response that is also able to neutralize the infectious activity of a virus or other pathogen from which the protein is derived.

A significant effort has been devoted to discovery of general rules which govern the selection of protein epitopes by the immune system and development of methodology for mimicry of such epitopes with synthetic immunogens. Evidence has emerged suggesting that linear or discontinuous epitopes may be recognized and that these may adopt defined conformational states that are not readily duplicated in a synthetic peptide. Attempts to devise conformationally restricted peptides as superior antigens have also been given serious attention. In such approaches the structural context of a peptide sequence within a protein antigen is considered in producing a suitable mimic. Typically, the epitope may adopt a secondary structure such as a β-turn or a-helix. A similar structure may be induced in a small peptide by intramolecular covalent modification between two residues that constrains its conformational freedom. These ordered structures can be important as B-cell determinants. However, they are insufficient immunogens in the absence of helper T-cell determinants. Recently developed peptide vaccine models have incorporated T-cell epitopes in association with the B-cell epitope. Designs include simple tandem linear synthesis of peptides as well as increased epitope valency through coupling T-cell and B-cell peptides to a branched polylysine oligomer. The latter assemblies, referred to as multiple antigenic peptides, have shown promise as vaccines against various pathogens.

Unlike the conformationally defined B-cell epitopes, sequences recognized by T-cells undergo extensive processing to short linear peptide fragments before they are bound to a major histocompatibility complex (MHC) for recognition at the surface of an antigen-presenting cell. This elaborate processing mechanism depends on intracellular proteolytic activity and translocation of the products to the cell membrane. Synthetic peptide immunogens may not effectively participate in this process, despite the presence of the T-cell epitope. The immunogenicity of the molecule can be expected to correlate with the efficiency of natural processing of the T-cell epitope. Studies with linear synthetic peptides indicated that chimeric peptides containing T-cell and B-cell epitopes were superior immunogens when the B-cell epitope was amino-terminal. However, the reverse orientation has also been reported to produce a stronger immune response. A general rule may not be obvious since natural antigen processing probably accepts various orientations, including internal epitopes that require multiple processing steps to release the peptide. Also the efficiency of a construct may depend on many other factors, such as molecular context and flanking sequences that affect processing or presentation and the overall nature of the immunogen which can affect the functional pairing between several available T-cell and B-cell epitopes.

Further limitations to the use of synthetic peptides as vaccines result from the genetic restriction to T-cell helper function. Multiple MHC class II molecules encoded within the genome of a species are subject to allelic exclusion. A specific T-cell epitope may interact with only one or a few alleles of the MHC. Therefore individuals may respond differently to the immunogen despite inclusion of T-cell helper epitopes. Vaccine development must overcome the MHC-restricted response to provide the broadest possible response in an outbred population. In the murine model the T-helper cell responses are MHC-restricted and major haplotypes H-2b, H-2k, and H-2d are represented in several inbred strains. Certain T-cell epitopes are known to be recognized in the context of multiple MHC class II alleles and can thereby provide "promiscuous" T-helper stimulation. A number of epitopes, such as from tetanus toxin, measles virus, and *Mycobacterium tuberculosis* have been reported to be universally immunogenic. These may have significant benefit for subunit vaccine design.

As an alternative to chemical synthesis, molecular biological techniques can provide significant advantages for production of polypeptides that display both B-cell and T-cell epitopes. Expression of proteins from cloned genes obviates burdensome peptide synthesis, purification and conjugation chemistry typically used in production of immunogenic materials. Furthermore, the stochastic chemistry for preparation of peptide-carrier conjugates is replaced by the defined chemical structure provided by the genetic fusion. Therefore the epitopes can be introduced in ordered structures that have optimal and reproducible immunogenic properties. Considerations that arise in the development of optimal designs can be addressed at the genetic level. Thus, definition of the target epitopes and their flanking sequences, relative orientation and conformations of these sequences within the larger polypeptide, and epitope copy frequency can be established in the gene design.

Several recombinant host proteins have been successfully utilized for immune presentation of peptide epitopes. The *E. coli* maltose-binding protein (MalE) has been used to study the influence of location and orientation of inserted T-cell epitopes. The major coat protein (pVIII) of filamentous bacteriophage fd has been used for display of HIV B-cell epitopes at the N-terminus. The recombinant phage particles evoked a strong antibody response in mice, which cross-reacted with HIV strains and which is also capable of neutralizing the virus. These approaches promise to enhance the potential of subunit or synthetic vaccine models.

SUMMARY OF THE INVENTION

The present invention relates to a variety of epitope-containing heat shock fusion proteins. In one embodiment, the heat shock protein-ubiquitin is fused to a variety of eptiopes or epitope-containing segments. The specific fusion architecture is described in detail below. The epitope-containing segments of the ubiquitin fusion protein comprise either a single epitope or a group of identical or non-identical epitopes.

The present invention also relates to DNA constructs which encode an epitope-containing heat shock fusion protein of the type described above, and to cells transformed with such expression constructs.

In other aspects, the present invention relates to methods for stimulating an immune response in an animal, the immune response being directed toward a heat shock fusion protein of the type described above. The heat shock fusion protein is administered to an animal under conditions appropriate for the stimulation of an immune response. In an alternative embodiment, a DNA construct encoding the heat shock fusion protein is introduced into cells, rather than the fusion protein directly.

The present invention also relates to methods for inducing the production of antibodies to endogenous biomolecules using a heat shock fusion protein as described above where the said peptide epitopes are, or are not, related to the endogenous biomolecules in chemical composition but are so called "mimics" of the biomolecular structure and as such have the ability to elicite antibodies to the said biomolecules. Such peptide (epitope) mimics are isolated typically by using phage peptide libraries.

The present invention also relates to methods for reducing levels of a predetermined protein (e.g., hormone(s)) in an animal relative to base-line levels, to methods for reducing endogenous TNF levels relative to those in a disease state, to methods for reducing the sperm count in males or inactivating sperm in men and women, to methods for reducing the allergic response, to methods for increasing the growth rate of an animal and to methods for the production and identification of antibodies for use in experimental or diagnostic samples.

DETAILED DESCRIPTION OF THE INVENTION

The present invention is based, in one aspect, on the discovery that a fusion protein comprising a heat shock protein (e.g., ubiquitin), fused to an epitope or epitopes in a defined manner, is useful for the stimulation of a highly specific immune response when administered to an animal. The specific fusion architecture encompassed by the invention will be discussed in greater detail below.

Heat shock proteins are proteins which are induced during a heat shock. Other stress stimuli are also known to induce a similar response. These proteins are produced to enable the cell to better stand the heat shock or stress. Under these conditions the pattern of gene expression changes and cells overproduce a characteristic set of proteins commonly referred to as heat-shock proteins (hsps). One factor in the induction of the heat shock response is the proteolysis of abnormal proteins.

Various examples of heat shock proteins exist. In yeast, mammals and other eukaryotes, ubiquitin is one of these proteins. Ubiquitin is known to be involved in an ATP-dependent pathway of proteolysis. It is also known that proteolysis is an important step in the production of peptides which function in development of the immune response to antigens. Thus it is recognized that hsps are ideal candidates for use in connection with vaccine development.

In connection with the present invention, ubiquitin is used as a scaffold to stabilize and display recombinant immunologically active heterologous antigens (referred to herein as epitopes), presumably in a form which generally approximates the native conformation of the epitope. This technique is sometimes referred to as conformational mimicry. Generally, the preferred size of the amino acid segments referred to in items a) and b) of the preceding paragraph range from about 5 to about 70 amino acid residues, although larger segments are not intended to be excluded by this statement of the preferred size range.

Ubiquitin is a small 76-residue single domain protein which does not induce an appreciable immune response when administered to an animal. Presumably, this "immunological silence" is based on the fact that ubiquitin is expressed in nearly identical form in all eukaryotic systems. Ubiquitin has a variety of other characteristics which make it an ideal "carrier" for the conformational mimicry approach. For example, ubiquitin is highly resistant to protease digestion and is extremely stable both in vivo and when stored for extended periods of time in vitro. The three-dimensional structure of ubiquitin has been determined by X-ray crystallography and its small size makes it amenable to molecular modeling. Additionally, ubiquitin fusions can be overexpressed in prokaryotic systems such as *E. coli*, in soluble form, and purified. One of skill in the art will recognize that for particular applications some of the aforementioned properties are unimportant and dispensable. At the present time, there is no comparable protein scaffold system available which offer the benefits of the ubiquitin system.

If epitopes are to be fused to the ubiquitin framework as outlined above, whether at a single location or non-contiguous locations, it is important to determine what types of ubiquitin modifications are tolerated. In this context, "tolerated" can have at least two meanings, systemic tolerance and functional tolerance. It should also be noted that the expression "fused", as used herein, means covalent bound by an amide linkage. This expression encompasses insertion, as well as substitution. At times, these expressions may be used interchangeably herein.

Systemic tolerance, (i.e., tolerance by the immune system) is important to ensure that the immune response is directed to the epitopes, and not to the ubiquitin carrier. Thus, epitope insertion should be designed such that changes to the secondary and tertiary structure of ubiquitin are minimized.

Ubiquitin functional tolerance refers to the ability of the ubiquitin protein to behave functionally in a manner analogous to wild-type ubiquitin. This functional tolerance can also be important in a variety of contexts. This property should also be maintained, at least in connection with certain applications, by the ubiquitin fusion carrier constructs of the present invention.

As disclosed herein, insertions at particular internal sites in ubiquitin are "tolerated", as this term is defined above. One advantage of using ubiquitin as an immunogenic display scaffold, particularly for an internally-fused epitope or epitopes, resides in its ability to maintain the secondary structure found in the epitopes native protein. These secondary structures include, for example, β-turns and α-helices. The-conformation of the epitope can be further modified by introducing intramolecular bonds between two residues of the epitope which results in conformational constraints on the overall structure of the epitope. The fusion of an epitope or epitopes to terminal regions of ubiquitin also offers advantages in connection with immune-stimulatory activities.

In a first embodiment, the present invention relates to a ubiquitin fusion protein comprising ubiquitin fused to a single epitope-containing segment: comprising two or more identical or non-identical epitopes, the epitope-containing segments being fused to ubiquitin at fusion sites selected from the group consisting of the N-terminus and an internal fusion site. As discussed in greater detail below, a variety of considerations are taken into account when selecting an epitope of use in connection with the fusion proteins of the present invention. Generally speaking, an epitope which can stimulate an immune response which protects against an infectious disease, an auto-immune disease or allergic reactions are candidate epitopes for use in connection with the present invention. Epitopes which do not fall into one of these categories can also be useful, and non-limiting examples are discussed more fully below.

With respect to the first embodiment, fusions at a single internal location in the ubiquitin moiety must be designed rationally to minimize, for example, adverse consequences with respect to ubiquitin structure and function. In light of the fact that fused epitopes must be "seen" by the immune surveillance system, it is also important that internally fused epitopes are exposed in the folded fusion protein, not buried within a hydrophobic domain. The plurality of epitopes can also be fused to ubiquitin at the N-terminus of the molecule. The epitopes can be identical or non-identical. In addition, the epitopes can be B cell epitopes, T cell epitopes or a mixture of B and T cell epitopes. For many applications, preferred epitopes are B-cell epitopes which are known to be a target for neutralizing antibodies.

A second embodiment of the present invention relates to a ubiquitin fusion protein comprising ubiquitin fused to two or more non-contiguous epitope-containing segments, each epitope-containing segment comprising one or more identical or non-identical epitopes. The non-contiguous locations where fusion is appropriate are internal locations within the ubiquitin moiety, or at the N- or C-terminus of the ubiquitin molecule.

As used herein in connection with the second embodiment, the term "epitope-containing segment" refers to a sequence of amino acids containing one or more epitopes. The epitopes within any particular epitope-containing segment can be identical, or non-identical. In addition, the epitopes in a particular epitope-containing segment can be B cell epitopes, T cell epitopes or a mixture of B and T cell epitopes. As discussed above, B-cell epitopes targeted by neutralizing antibodies are preferred in some contexts.

When considering the insertion of epitopes within the ubiquitin molecule, the structure of the ubiquitin molecule must be considered. The prominent structural features of ubiquitin, as determined by X-ray crystallography (see, e.g., Vijay-Kumar et al., *Proc. Natl. Acad. Sci. USA* 82: 3582 (1985); Vijay-Kumar et al., *J. Mol. Biol.* 194: 525 (1987); and Vijay-Kumar et al., *J. Biol. Chem.* 262: 6396 (1987)) include a mixed β-sheet comprising two parallel inner strands (residues 1-7 and 64-72), as well as two antiparallel strands (residues 10-17 and 40-45). In addition, an α-helix (residues 23-34) fits within the concavity formed by the mixed β-sheet.

The amino acid sequences which link the structural elements defined in the preceding paragraph are referred to herein as "loop regions". Thus, loop regions can be defined as domains of ubiquitin which link either two strands within a β-sheet or a strand of a β-sheet and an α-helix. Insertions and substitutions can be made within these loop regions without disrupting the integrity of the ubiquitin molecule or abolishing the features which make ubiquitin a useful carrier for the display of constrained epitopes. Insertions and substitutions within these loop regions tend not to alter the relationships between the prominent structural features defined in the preceding paragraph. Rather, the epitopes introduced into these loop regions tend to protrude from the compact globular ubiquitin structure thereby exposing these epitope residues such that they are easily recognizable by lymphocytes, for example.

As discussed above, internal modification sites are selected such that the ubiquitin secondary structure is maintained and the conformation of the inserted epitope is constrained. Epitopes can also be joined to ubiquitin as extensions of the C-terminus. Epitopes fused to the C-terminus of ubiquitin can be cleaved off by ubiquitin-specific proteases in vivo or in vitro. This allows the peptide to be administered to a cell as part of a larger fusion protein which is both easier to purify and handle as compared to free epitope. Following cellular uptake, the epitope attached to the ubiquitin can be cleaved from the C-terminus of ubiquitin and associated with a surface protein such as the MHC complex for expression on the cellular membrane.

In another embodiment, the subject invention relates to a ubiquitin fusion protein comprising ubiquitin fused to a single epitope-containing segment, the epitope-containing segment comprising two or more identical or non-identical epitopes. The epitope-containing segment can be fused to ubiquitin at its N-terminus, terminus or internally.

The invention relates to yet another fusion protein embodiment comprising ubiquitin fused to a single epitope-containing segment comprising one or more identical or non-identical epitopes. In this embodiment, the epitope-containing segment is fused to the ubiquitin moiety at the N-terminus of ubiquitin.

The use of ubiquitin fusion proteins to initiate a humoral response is described in more detail in the following Exemplification section. More, specifically, these experiments demonstrate, for example, that the B-cell and T-cell epitopes expressed in the ubiquitin fusion protein stimulated targeted immune-responses. Further, the experiments demonstrate that a humoral immune response to an internally inserted B-cell epitope was enhanced by the addition of a T-cell epitope to the C-terminus of the ubiquitin fusion protein. Although the bulk of the in vivo data reported herein were generated in experiments employing murine indicator assays for the generation of antibodies against the ubiquitin fusion proteins, the fundamental principles are applicable to humans as well as other animals. Given the disclosure of the subject application it is a matter of routine experimentation to select epitopes of interest and incorporate such epitopes of interest into a ubiquitin fusion protein for use as an immunogen.

Thus, in a preferred embodiment, the ubiquitin fusion protein comprises an internally inserted B-cell epitope and a T-cell epitope joined to the C-terminus of ubiquitin one of skill in the art can identify B-cell epitopes which have the ability to drive a strong humoral immune response following administration to an animal. The B-cell epitope which is selected will depend upon the intended use of the ubiquitin fusion protein. For instance, if the ubiquitin fusion protein is to be used as a vaccine, the B-cell epitope can be derived from a protein which is expressed by a virus, bacteria or other infectious organism associated with causing a disease. The protein which is selected should be one which contains epitopes which elicit strong antibody responses. These responses are associated with protection of the animal species from the symptomology caused by the infectious organism. Preferably, the B-cell epitope which is selected is derived from a portion of the protein from the infectious organism known to be both highly immunogenic and to which protective antibodies can be produced. In general, this will include proteins found on the surface of the infectious organism which are involved in binding and to which antibodies have a high degree of access.

One example of a B-cell epitope which fulfills the requirements set forth above is the V3 loop of the HIV gp120 glycoprotein. As described in the following section, an epitope derived from the V3 loop of the HIV gp120 glycoprotein, when internally inserted within a ubiquitin fusion protein, is able to drive a strong humoral response. In fact, the antibody response was stronger than that found when the epitope was administered independently as a peptide antigen. The selection of this epitope was based on extensive data showing it is a target of neutralizing antibodies.

The selection of the B-cell epitope is not limited to proteins associated with infectious organisms. For instance, as shown in Example 2 below, when the ubiquitin fusion protein contains an internally inserted epitope from a prostate-specific antigen, a strong antibody recognition was detected. Examples of other epitopes useful in connection with the present invention include those from proteins which are commonly used as immunological "carriers" as part of experimental studies. These include hen egg lysozyme, keyhole limpet hemocyanin and ovalbumin. One of skill in the art will recognize that any protein containing a B-cell epitope which is capable of driving a humoral immune response can be included in a fusion protein of the present invention. Many such epitopes are known and others can be determined through routine experimentation.

In a preferred embodiment, a T-cell epitope is joined to the C-terminus of the ubiquitin fusion protein. This epitope is selected based on its ability to enhance the humoral immune response directed to the internally inserted B-cell epitope when both are placed in their proper orientation with respect to ubiquitin. The preferred T-cell epitope is selected from a group of T-cell epitopes which are able to elicit "promiscuous" T-cell help. This type of T-cell epitope is-commonly referred to as a universal epitope. Universal T-cell epitopes function by stimulating helper T-cells specific to the B-cells responsive to the ubiquitin fusion protein containing the internally inserted B-cell epitope. They do this regardless of the subject's MHC haplotype or whether the specific "target" protein is different than the protein the universal T-cell epitope is derived from. Examples of universal T-cell epitopes include epitopes from tetanus toxin, measles virus and *Mycobacterium tuberculosis*. This list of universal T-cell epitopes is not intended to be comprehensive, others which are known or can be determined through application of routine experimentation are also included.

To stimulate cytotoxic T-cells as part of a cellular immune response, T-cell epitopes are preferably inserted internally within the ubiquitin moiety. In addition, it is preferable to fuse at least one T-cell epitope to the C-terminus of the ubiquitin fusion protein. In this case, the T-cell epitopes are selected on the basis of their ability to ensure stimulation of cytotoxic T-cells specific for the particular epitope. However, a universal T-cell epitope can be attached to the C-terminus of the ubiquitin fusion protein to enhance the stimulation of the specific T-cell response.

Cytotoxic T-cells play an important role in the surveillance and control of viral infections, bacterial infections, parasitic infections and cancer, for example. Vaccination with synthetic epitopes, or with epitope pulsed cells, has been shown to induce specific cytotoxic T-cell responses directed against immunogenic viral or tumor-derived epitopes. Alternative protocols of T-cell activation allow the triggering of more selective cytotoxic T-cell responses with greater therapeutic effectiveness.

Generally, the fusion of peptides to the C-terminus of ubiquitin generates a construct which is cleavable, in vivo, by ubiquitin-specific proteases. It is well-established that such ubiquitin-specific proteases cleave ubiquitin fusions after a C-terminal residue (residue 76), thereby releasing the C-terminal peptide. The present invention also encompasses ubiquitin fusion proteins which have been modified such that the fusion is not efficiently cleaved by ubiquitin-specific proteases. As is well known to those of skill in the art, ubiquitin can be made resistant to ubiquitin-specific proteases by altering residues at the C-terminus of ubiquitin. For example, by altering the identity of the amino acid at position 76 of ubiquitin (e.g., from glycine to valine or cysteine), the rate of cleavage of a C-terminal ubiquitin fusion can be substantially reduced to the point where cleavage can not be detected using the assays typically employed for monitoring such cleavage.

As mentioned previously, the present invention also encompasses fusions to the N-terminus of ubiquitin. It is noted that fusion proteins in which an epitope or epitopes are attached to the N-terminus ubiquitin must be designed such that the N-terminal residue of the encoded fusion protein is methionine. If the N-terminal residue is a residue other than methionine, initiation of translation does not occur efficiently. Unfortunately, however, previous studies have demonstrated that fusions of this type can reduce antibody binding or elicit the production of antibodies of low affinity for the epitope fused to the N-terminus of ubiquitin.

To overcome this problem, a tandem ubiquitin fusion is created by attaching a second ubiquitin protein to the N-terminus of the epitope or epitopes attached to the N-terminus of the first ubiquitin moiety. Thus, in this embodiment of the present invention, two ubiquitin molecules flank an epitope or epitopes. The C-terminus of the N terminal ubiquitin protein is of the wild-type sequence such that it is cleavable by ubiquitin specific proteases. DNA encoding this tandem ubiquitin fusion is used to transform either prokaryotic or eukaryotic cells. Previous work has shown that the tandem ubiquitin fusion is produced at an equivalent or increased level as compared to the single ubiquitin fusion proteins.

Following purification, the tandem ubiquitin fusion can be cleaved, in vitro, by a ubiquitin specific protease thereby releasing the N terminal ubiquitin protein from the core fusion protein which is comprised of an epitope attached to the N-terminus of the C terminal ubiquitin protein.

The C terminal ubiquitin protein in the tandem ubiquitin fusion protein can be modified by the inclusion of other epitopes in a manner consistent with the description of the invention above. Thus, fusion can be made within the C terminal ubiquitin molecule or to the C-terminus of the C terminal ubiquitin molecule.

An alternative tandem ubiquitin construct suitable for use in connection with all embodiments of the present invention is encompassed within the scope of the present invention. More specifically, in the alternative tandem ubiquitin construct, the two ubiquitin moieties are contiguous (i.e., the N-terminus of a first ubiquitin moiety is joined to the C-terminus of a second ubiquitin moiety). In this embodiment, the N-terminal residue of the first ubiquitin moiety is a residue other than methionine. This first ubiquitin moiety is then fused to a wild-type ubiquitin moiety which is cleavable by a ubiquitin-specific protease.

Alternatively, the second ubiquitin moiety in this tandem construct need not be a complete ubiquitin moiety. Rather, a C-terminal subdomain of ubiquitin competent to direct cleavage by a ubiquitin-specific protease, is sufficient. In addition, in connection with this and any other embodiment of the present invention, ubiquitin (or portions thereof) may be modified to inhibit cleavage by a ubiquitin-specific protease.

A variant of one of the two major embodiments of the present invention is a ubiquitin fusion comprising a first and a second epitope-containing segment inserted internally, and a third epitope-containing segment fused to the C-terminus of ubiquitin. The subject invention encompasses a wide range of such variant embodiments. There is no theoretical limit on the number of epitopes which can be inserted within or fused to the N and C-terminus of a ubiquitin fusion protein.

In preferred embodiments, internally fused epitopes are fused as single epitopes, non-contiguously. This design ensures that antibodies produced following vaccination are specific for a single epitope and do not cross-react with other epitopes which have also been internally fused to ubiquitin. Thus, each epitope elicits a specific antibody response by producing antibodies which do not cross-react with other epitopes contained within the same ubiquitin fusion protein. The use of an epitope-containing segment in which two or more distinct epitopes are displayed is preferred when attempting to create bifunctional antibodies for experimental, diagnostic or therapeutic uses.

In another embodiment of the present invention, an epitope-containing ubiquitin fusion protein is modified by conjugation to a carrier protein such as ovalbumin (OVA) or keyhole limpet hemocyanin (KLH). Example 5, presented below, exemplifies such an embodiment.

Ubiquitin fusion proteins of the type described above can be modified post-translationally by the addition of fatty acids to enhance immunogenicity. For example, palmatic acid ($C_{16}$) can be added using appropriate chemistry for this purpose.

The discussion above has focused on a wide variety of epitope-containing ubiquitin fusion proteins. The invention also relates to DNA expression constructs which encode such epitope-containing ubiquitin fusion proteins. These constructs can be based on prokaryotic expression vectors or eukaryotic expression vectors. Many examples of such expression vectors are known in the art. Prokaryotic expression vectors are useful, for example, for the preparation of large quantities (e.g., up to milligram quantities) of the ubiquitin fusion protein. Eukaryotic expression vectors are useful, for example, when the addition of carbohydrate side chains (i.e., glycosylation) is important. The carbohydrate side chains can affect the properties of a protein in a variety of ways including, for example, the ability of the protein to function in vivo or in vitro; the ability of the protein to form a complex and associate with other proteins or nucleic acids; and the ability of the protein to bind to an antibody or other molecules specific for the protein of interest.

In another aspect, the present invention relates to methods of vaccination. The vaccine can be used to drive a cellular and/or humoral immune response depending on the type of epitopes fused to the ubiquitin fusion protein. The therapeutic amount of the ubiquitin fusion protein given to an animal species will be determined as that amount deemed effective in eliciting the desired immune response. The ubiquitin fusion protein is administered in a pharmaceutically acceptable or compatible carrier or adjuvant.

Thus, the present invention also encompasses pharmaceutical compositions for the administration of ubiquitin fusion proteins. Examples of specific diseases which can be treated in this manner include, for example, gastrointestinal diseases, pulmonary infections, respiratory infections and infection with HIV. The pharmaceutical compositions are prepared by methods known to one of skill in the art. In general, the ubiquitin fusion protein is admixed with a carrier and other necessary diluents which are known in the art to aid in producing a product which is stable and administrable. Administration of the pharmaceutical composition can be accomplished by several means known to those of skill in the art. These include oral, intradermal, subcutaneous, intranasal, intravenous or intramuscular.

Conventional vaccination methods involve the administration of an epitope-containing protein. Recently, and alternative to conventional vaccination methods, referred to as DNA vaccination, has been developed. In this method, DNA encoding the epitope-containing protein is introduced into the cells of an organism. Within these cells, the epitope-containing protein is directly expressed. Direct expression of the ubiquitin fusion proteins of the present invention by endogenous cells of a vaccinated animal allows for the continual stimulation of humoral and cellular immune responses over an extended period of time. This is in contrast to standard immunization protocols whereby the vaccine is injected at a single site one or more times. Following injection, the vaccine is disseminated to lymphoid organs where a single immune response occurs.

Direct expression can be accomplished by introducing DNA constructs which encode the desired ubiquitin fusion protein into the cells of an animal. The constructs typically contain promoter elements and other transcriptional control elements which direct the expression of the ubiquitin fusion protein. Introduction of the DNA construct can be by any conventional means including direct injection. The preferred administration site is muscle tissue or tissues rich in antigen presenting cells.

The introduction of a ubiquitin fusion protein as described above can also induce a tolerizing effect on the humoral or cellular immune response in an animal. Tolerization occurs following delivery of the ubiquitin fusion proteins to T-cells. The induction of a tolerization response is useful, for example, in connection with the treatment of allergic or autoimmune disorders. Examples of epitopes which can be used in a therapeutic regimen designed to induce tolerization include the Fel d 1 peptides, which are the major allergens found in cat pelts. These peptides can be internally inserted, for example, and fused to a cleavable C-terminus of ubiquitin. Typically patients to be treated are dosed subcutaneously with the ubiquitin fusion proteins once per week for several weeks. However, dosing can also be done orally or intranasally over a similar length of time. The result is a reduction of the allergic and/or autoimmune responses. These ubiquitin fusion proteins can also be given orally.

The use of ubiquitin as a scaffold for the presentation and stimulation of immune responses also allows the stimulation and generation of anti-self responses. An example of a potentially valuable anti-self response is the generation of anti-GnRH (gonadotrophin releasing hormone) antibodies. As described in Example 3 below, efforts have been made to generate immunogens which stimulate a strong anti-GnRH response which results in the suppression of luteinizing hormone (LH) and follicle stimulating hormone (FSH) and indirectly suppresses the production of the steroidogenesis and gamete maturation in both males and females. The value of this type of anti-self response in humans lies in the treatment of prostate cancer and breast cancer.

In livestock and pets, the ability to stimulate an anti-self response provides a simple alternative to physical castration. Previous work employing complex immunogens has demonstrated varying degrees of success in immunological castration. However, the production of complex immunogens is cumbersome, typically involving a combination of synthetic chemistry, expensive HPLC purifications, and chemical coupling methods. The use of ubiquitin fusion proteins containing. GnRH epitopes facilitates the production of inexpensive and potent immunogens for use in connection with immunocastration. In particular, ubiquitin fusions which include the peptide QHWSYGLRPGQHWSYGLRPGQHWSYGLR-PGQHWSYGLRPGC SEQ ID NO: 36 are of interest.

Immunocastration of pigs is especially valuable since it does not result in the detrimental side-effects associated with physical castration. More specifically, physical castration of pigs typically results in animals which do not grow as well as normal animals. In addition, physically castrated pigs tend to have a higher fat percentage than non-castrated pigs. Since, immunocastrated animals are not castrated as early as those which undergo normal physical castration, a farmer can take advantage of the growth rates found with non-castrated animals. Finally, by immunocastrating, the farmer avoids the production of unpalatable meat found with uncastrated male pigs.

Other examples of self proteins which could be used with ubiquitin to generate vaccines able to modulate the hormones, cytokines and physiology of humans and animals are: growth hormone and its peptides to modulate growth both negatively and positively; TNF and its epitopes to modulate septic shock, arthritis, inflammatory bowel disease, crohn's disease, and ulcerative colitis; immunoglobulin epsilon heavy chain for the control of allergic reactions; chorionic gonadotrophin for fertility control; inhibit for fertility control; and Sperm proteins such as sp 17 (for example amino acids 4-19 and 118-127) and the 71kd sperm protein for control of fertility both in men and in women.

A further use of ubiquitin as a scaffold is as part of a vaccine to enhance the growth rate and thereby the final weight of livestock prior to shipment to market. This type of vaccine offers a cost effective means to increase the value of livestock such as pigs, cattle and other commonly raised animals. Presently, to increase the weight of livestock several methods are being utilized. Amongst these methods, the addition of antibiotics to the feed has become very common. However, while addition of antibiotics to feed is cost effective, it has limitations. For instance, it has been blamed for an increase in the creation of antibiotic resistant strains of bacteria.

An alternative means to increase the growth rate of livestock which does not result in detrimental side-effects is through vaccination of the animals with an epitope of growth hormone which is part of a ubiquitin fusion protein. The result of this vaccination is an increase in the activity of the animals endogenous growth hormone. The vaccine is created by inserting an epitope from the growth hormone protein (e.g., amino acids 54-95) into the ubiquitin protein thus creating a ubiquitin-growth hormone fusion protein. The effective use of this type of vaccine is described in Example 7 below. More specifically, following the injection of a vaccine comprised of adjuvant and a ubiquitin fusion protein containing the growth hormone protein epitope, the growth rate of pigs was improved when compared to control pigs which received either adjuvant only or adjuvant and ubiquitin only.

In addition to the uses described above, the ubiquitin fusion proteins of the present invention can be used for the identification of antibodies from experimental or clinical samples. Antibodies to be assayed can be found, for example, in blood, fecal material, the linings of mucosal associated lymphoid tissues, cellular biopsies and other sources known by one of skill in the art to contain at least a minute quantity of antibody. Assays for which the ubiquitin fusion proteins are well suited include ELISAs, radioimmunoassay as well as other commonly used competition assays. These types of assays are useful in identifying antibodies from an experimental or clinical sample which have specificity to at least one epitope of a known protein. In general, the assays involve mixing a predetermined aliquot of the ubiquitin fusion protein with a series of dilutions of the experimental or clinical antibody sample. This is followed by detection of the antibodies which bind to the ubiquitin fusion protein.

Detection can be accomplished by various means, but for the present invention, a labeled detection antibody is preferable. For example, if the experimental or clinical antibody sample is from a human, the detection antibody can be a polyclonal antibody with specificity for the human heavy chain portion of the sample antibody. The detection antibody is attached to either an enzymatic label, a radioactive label or a fluorochromatic label. Examples of commonly used enzymatic labels are horse radish peroxidase and alkaline phosphatase. A standard radioactive label includes iodine 131. Fluorochromatic labels include fluorescein and Texas red. The method of visualization of the complex containing the ubiquitin fusion protein, the sample antibody, and the labeled antibody depends on the label attached to the antibody and would be known to those of skill in the art.

EXAMPLES

No. 1

Fusion proteins consisting of short peptide sequences inserted within a ubiquitin scaffold were developed and tested as immunogens for eliciting a targeted immune response. Preparation and testing of the fusion proteins required several steps including: (I) the design and construction of plasmids encoding peptide sequences fused to the ubiquitin polypeptide at two permissive sites which could be useful for epitope display; (II) the high-level expression in *E. coli*, purification and characterization of the expected ubiquitin fusions; and (III) evaluation of the immune response in mice with regard to immunogenicity, antibody specificity, cross-reactivity and helper T cell response. Fusion proteins were developed to display the sequence of the HIV-1 gp120 V3 loop, the principal recognition determinant of virus neutralizing antibodies.

Materials and Methods

Mice

BALB/c, C57BL/6 and C3H/HeN female mice at 6-8 weeks of age were obtained from Charles River (Frederick, Md.) or Jackson Labs. Animals were housed and cared for in an IACUC supervised facility in accordance with an NIH approved Animal Welfare Assurance.

Peptides, Proteins and Antibodies

Bovine ubiquitin (Sigma, St. Louis Mo.) was dissolved in PBS and filtered through a 0.2 micron filter. Goat anti-mouse peroxidase conjugate was used as obtained from Promega. Mouse monoclonal antibodies against V3 peptides of gp120MN (HG-1) and gp120IIIB (#13-105-100) were purchased from Biodesign International (Kennebunk, Me.) and from Advanced Biotechnologies Inc. (Guilford, Md.) respectively. Recombinant proteins gp120IIIB and gp120MN and a 36 residue "universal" V3 peptide CTRPNNNTRKSIHIG-PGRAFYTTGEIIGDIRQAHC (SEQ ID NO:1) were obtained from Intracel Corporation (Cambridge, Mass.). Synthetic peptides KRIHIGPGRAFYTTK (L-V3) (SEQ ID NO:2) and CKSIHIGPGRAFYTTGC (C-V3) (SEQ ID NO:3) were obtained through the AIDS Research and Reference Reagent Program, Division of AIDS, NIAID, NIH: from Peptide & Protein Research Consultants (Exeter, Devon, UK).

Oligonucleotide Design

Oligonucleotides were obtained by custom synthesis through Bioserve Biotechnologies. Sequences shown below were designed to encode peptide sequences and to provide appropriate complementary overhangs for ligation to restriction sites in plasmids. Oligonucleotides were treated with T4 polynucleotide kinase and complementary pairs were annealed by heating to 65EC for 5 minutes, then cooling to room temperature over 30 minutes.

```
A 5'-TTAAGACTGCGTGGCGGCGACCA       (SEQ ID NO: 4)
   GGTTCACTTCCAGCCGCTGCCGCCGGC-3'

B 5'-TGTTGTTAAACTGTCTGACGCTC       (SEQ ID NO: 5)
   TGTAAGCTTCTGCA-3'

C 5'-GAAGCTTACAGAGCGTCAGACAGTTTA   (SEQ ID NO: 6)
   ACAACAGCCGGCGGCA-3'

D 5'-GCGGCTGGAAGTGAACCTGGTCGCC     (SEQ ID NO: 7)
   GCCACGCAGTC-3'

E 5'-TTAAGACTGCGTGGCGCTGACCAGGTTC  (SEQ ID NO: 8)
   ACTTCCAGCCGCTGCCGCCGGC-3'

F 5'-GCGGCTGGAAGTGAACCTGGTCA       (SEQ ID NO: 9)
   GCGCCACGCAGTC-3'

G 5'-AAGAAATCCACATCGGTCCGGGTCGTGC  (SEQ ID NO: 10)
   TTTCTACACCACCATCCCGCCGGATCA-3'

H 5'-ATCCGGCGGGATGGTGGTGTAGAAAGCA  (SEQ ID NO: 11)
   CGACCCGGACCGATGTGGATTTCTTT-3'

I 5'-TTAAGACTGCGTGGCGG             (SEQ ID NO: 12)
   CATCCACATCGGTCCG-3'

J 5'-GGTCGTGCTTTCTACAC             (SEQ ID NO: 13)
   CACCTAACTGCA-3'

K 5'-GTTAGGTGGTGTAGAAAGC           (SEQ ID NO: 14)
   ACGACCCGGACCGAT-3'

L 5'-GTGGATGCCGCCACGCAGTC-3'       (SEQ ID NO: 15)
```

Strains and Vector Construction

Ubiquitin fusions were cloned-and expressed in the Proteinix proprietary E. coli strain DH5α F' IQ™ (Life Technologies). Vector constructs for expression of fusion proteins are derivatives of pDSUb (provided by M. Rechsteiner, Univ. of Utah), which is a derivative of pDS78/RBSII. The ubiquitin codon usage was optimized for expression in E. coli. Transformants containing pDSUb or its derivatives were selected for ampicillin resistance. Ubiquitin fusion expression, under control of the lac promoter, is inducible by addition of IPTG. Cloning at the ubiquitin codon 35 was initially performed in pRSETUb, derived from pRSET (Invitrogen, Inc.) by subcloning of the ubiquitin gene from pDSUb to pRSET utilizing the Nde I and Hind III restriction sites. Restriction sites for insertions at codon 35 of ubiquitin were created by in vitro mutagenesis with a synthetic oligonucleotide using the MORPH mutagenesis kit (5 Prime-3 Prime, Inc.) to obtain pPX153. Digested vector fragments were treated with calf intestinal alkaline phosphatase and purified from agarose gel slices after electrophoresis using the Geneclean kit (Bio 101). Vector fragments and double stranded oligos were ligated and products were used for cloning in E. coli strain DH5aF'IQTM (Life Technologies. All restriction digests, ligations and transformation of E. coli were done according to standard manipulations using commercial DNA modifying enzymes as instructed by the manufacturer (New England Biolabs). Correct cloning of the oligonucleotide insertions was confirmed by DNA sequencing using the Sequenase Version 2.0 kit (USB, Cleveland, Ohio).

Expression, Purification and Characterization of Fusion Proteins

Cell paste from bacterial fermentation was resuspended in lysis buffer (5 ml/g wet paste) with vortexing. General purpose buffer consisted of 20 mM MES pH 5.5, supplemented with 1 mM PMSF, 0.5 mM ZnCl2. Cultures expressing certain fusion proteins were lysed in 50 mM acetate pH 4.0 (UbaMT) or pH 4.5 (UbgMT). Cells were disrupted by sonication on ice 2×4 min with a 50% duty cycle. Homogenates were centrifuged at 15,000×g, 45 min, 4EC. The supernatants were further diluted with 3 volumes of lysis buffer, filtered through a 0.45 Fm filter, and loaded onto a 30 mL SP sepharose HP ion exchange column at a linear flow rate of 1.4 cm/min. The fusion protein was eluted by a NaCl gradient (0-0.5 M) over 16 column volumes. Fractions were assayed by SDS-PAGE on 10-20% tricine gels (Novex, San Diego Calif.) and protein concentration was determined by the BCA method (Pierce Co.) using a ubiquitin standard curve. Peak fractions were pooled and evaluated further by C18 reversed phase HPLC on a Vydac 218TP54 column using a gradient of 30-45% acetonitrile in water containing 0.1% TFA over 7 min at 1.00 mL/min, with UV detector set at 214 nm.

Immunoblots were prepared by electroblotting of samples from SDS-PAGE gels onto Immobilon-P membrane (Millipore Corp.) using an X-Cell II Blot Module (Novex). The membranes were incubated in PBS containing 4% dry milk overnight and then washed with PBS. Incubations with primary antibody were done in PBS, 0.1% Tween 20 for 2 hr at room temperature. After 3 washes with the dilution buffer, membranes were incubated with goat anti-mouse IgG HRP conjugate at 1:5000 dilution in the same buffer. The wash steps were repeated and the membrane was developed with ECL Western detection reagents kit (Amersham, Waltham, Mass.) according to the manufacturer's instructions.

In vitro Cleavage of Ubiquitin Fusion Proteins by UBP

Reactions of UbV3gMT, UbgMT and UbaMT were monitored by C18 reverse phase HPLC on a Vydac 218TP54 column with detection at 214 nm using a 10 min gradient of 20-50% acetonitrile in water containing 0.1% TFA, and by SDS-PAGE on 10-20% tricine gels. Aliquots of fusion protein (100-200 Fg) were diluted into 200 FL of 50 mM Tris pH 8.0, 5 mM DTT, 1 mM EDTA. A 1 Fl aliquot of UCH-L3 (2 ug) or reaction buffer (control) was added and the samples were incubated at 37EC and monitored over 1 hr by HPLC. SDS-PAGE samples were run after 2 hrs reaction time.

For large scale digests, purified UbgV3 from SP sepharose HP ion exchange was concentrated 3-fold by Centriplus 3 membrane concentrators. The final concentration of fusion protein was 2.1 mg/ml. The fusion protein in 12 ml of buffer was buffered with 631 Fl of 1 M Tris pH 8.0, 64.8 uL 1 M DTT, 24.0 uL 0.5 M EDTA. UCH-L3 (0.24 mg in 120 Fl) was added and the reaction was incubated at room temperature and monitored by HPLC. The product peptide peak was purified by semi-preparative C18 HPLC (Vydac 218TP510 1.0 cm diameter column) and lyophilized to yield the V3 peptide IHIGPGRAFYTT (SEQ ID NO:16). Identity was verified by FAB-MS. The MT peptide DQVHFQPLPPAVVKLSDAL (SEQ ID NO:17) was obtained by a similar procedure from ion exchange purified UbgMT (4.82 mg/ml). The peptide product was isolated from semi-preparative C18 HPLC using a 20-40% gradient of acetonitrile in 20 mM potassium phosphate, pH 6.0 over 8 min. The peptide content in the lyophilized product was estimated at 10% by weight based on HPLC peak area.

Immunization Protocols and Mouse Lymphocyte Proliferation Assay

Mice were inoculated in groups of 3 to 5 per antigen by an initial subcutaneous (s.c.) injection of 100 Fg of proteins in PBS emulsified in an equal volume of complete Freund's adjuvant (CFA) or incomplete Freund's adjuvant (IFA). Booster injections of proteins (100 Fg) were delivered intraperitoneal in IFA 3 weeks and 7 weeks later. Blood samples were collected at 4 weeks, 6 weeks, 8 weeks and 10 weeks from the initial injection. Serum was separated and diluted in PBS.

For preparation of sensitized T cells, mice were immunized in groups of 3 by injection s.c. in footpads with 50 Fg of proteins in PBS emulsified in IFA. Eight to ten days later mice were sacrificed and popliteal lymph nodes (LN) were removed aseptically. LN cell suspensions in RPMI 1640 were prepared as described and dispensed into 96-well plates at 5×105 cells per well. Antigens or peptides were added in triplicate wells and plates were kept in a CO2 incubator at 37EC for 4 days. Wells were then pulsed with 3H-deoxythymidine (1 FCi/well) and cells were harvested on filter pads 24 hours later using an automated collecting device. Filter sheets were allowed to dry and then counts were read on a Wallac microbeta plate reader (Wallac, Inc., Gaithersburg Md.). Stimulation was expressed as the average signal of duplicate or triplicate wells corrected for mean background counts (c.p.m. with protein or peptide—c.p.m. with buffer added).

Immunoassays

Fusion proteins (50 Fg/ml) or synthetic peptides (10 Fg/ml) in PBS were dispensed into immunosorbent 96-well plates (0.1 ml/well, Corning high binding flat bottom plates) and incubated for 1 hour at 37EC. Excess antigen was shaken out and nonspecific sites were blocked by addition of PBS containing 10 mg/ml of BSA (0.1 ml/well, incubated 30 min at 37EC). Plates were washed three times (Tris buffer 10 mM, 0.1% Tween 20, pH 8) and serially diluted serum samples (1/103-1/104 in PBS supplemented with 1% BSA) were added (0.1 ml/well). After 1 hour at 37EC plates were washed as before and developed with affinity purified goat anti-mouse IgG-horse radish peroxidase conjugate (0.5 Fg/ml in PBS supplemented with 1% BSA, 0.1 ml/well). After washing, bound enzyme was detected with o-phenylenediamine (1 mg/ml in phosphate-citrate buffer, 0.05 M, 0.02% H2O2, pH 5). Plates were read at 450 nm on a 96-well plate reader (Titertek). Titers are expressed as the dilution of serum giving an absorbance reading of 0.3 or 15% of the maximum reading.

Solution phase binding assays were performed by incubating peptides or proteins at concentrations ranging from 0.5-50 Fg/ml with antiserum in 0.1 M potassium phosphate, 2 mM EDTA, 10 mg/ml BSA, pH 7.8 at a fixed concentration of 2-fold greater than the previously determined titer dilution. Samples were incubated at 37EC for 2 hours, then applied to antigen-coated ELISA plates. The standard ELISA procedure was followed to determine the concentration of unbound antibody relative to samples containing no added ligand.

Results

Plasmid Construction and Sequences

Sequences of the oligonucleotides encoding for peptide inserts and their letter designations are given above. Linearized DNA from pDSUb restriction digested with Afl II and Pst I was ligated to double-stranded oligos A/D and B/C to obtain pDSUbgMT. Similar ligation to oligos E/F and B/C provided pDSUbaMT. Double stranded oligos G/H were ligated to the 1.2 kb and 1.6 kb fragments obtained from digest of pPX153 with restriction enzymes Xcm I and Bpm I to provide the V3 insertion at codon 35 of ubiquitin.

The new vector pRSETUbV3 was digested with Bgl II and Afl II, and the smaller fragment encoding UbV3 was gel purified. Ligation of this fragment to pDSUb, pDSUbgMT or pDSUbaMT, each digested with Bgl II and Afl II, generated expression vectors pDSUbV3, pDSUbV3gMT, and pDSUbV3aMT respectively. These were used to express the internal UbV3 fusion and double epitope fusions with a 19-residue C-terminal extension DQVHFQPLPPAVVKLSDAL (MT sequence) (SEQ ID NO:17) and either native (RGG) or mutant (RGA) protease recognition site at the ubiquitin C-terminus. A vector encoding ubiquitin fusion with a C-terminal 12-residue V3 sequence was assembled as follows: pDSUb was digested with Afl II and Pst I and the product ligated to paired oligos I/L and J/K to obtain pDSUbV3c.

Expression Yield and Purification

Fermentations in 10 L batches provided 150-175 g of wet cell paste. Fusion protein yields after a single ion exchange chromatography step ranged from 185 mg to 336 mg per 15 g of cell paste, equivalent to 1 L of culture. Product was isolated from 1-2 L shaker flask cultures (UbgV3) with similar results and yields. Fusion proteins UbgMT and UbaMT required chromatography with 50 mM acetic acid pH 4.0 and pH 4.5, respectively for retention on the ion exchange matrix. Ubiquitin fusions purified by ion exchange were greater than 98% pure as judged by SDS-PAGE.

In vitro Cleavage of C-terminal Ubiquitin Fusions with UCH-L3

Processing of ubiquitin fusion polypeptides by the ubiquitin C-terminal hydrolase UCH-L3 is presumed to depend on recognition of the native structure of the ubiquitin domain. Analytical digests of UbV3gMT and UbgMT by UCH-L3 proceeded with similar efficiency as shown by the HPLC and SDS-PAGE results. Cleavage of the UbV3gMT having an internal fusion in the ubiquitin sequence suggests that an insert in the 34-40 loop does not interfere with folding of ubiquitin or recognition by the enzyme. The reaction can be followed by the formation of peptide product detected by HPLC analysis. SDS-PAGE analysis is useful for determining completion by depletion of substrate and formation of a band corresponding in size with ubiquitin.

The enzymatic digest of ubiquitin fusions is a practical bioprocess for production of peptides. Two short peptides, IHIGPGRAFYTT (SEQ ID NO:16) and DQVHFQPLPPAV-VKLSDAL (SEQ ID NO:17), useful in this study, were conveniently prepared by processing of recombinant C-terminal ubiquitin fusions.

Binding and Specificity of Anti-V3 Peptide Antibodies to UbV3

Antibodies that neutralize HIV-1 infectivity are directed against the V3 loop or principal neutralizing determinant (PND) of gp120. The PND is implicated in several viral mechanisms known to evade the humoral immune response. Subunit vaccines based on the native structure in gp120 indicate only weak immunogenicity toward this region. Variability of the V3 loop in divergent viral isolates and depletion of B-cells producing antibodies to the PND in infected individuals could also allow for HIV-1 escape from immune surveillance. The gp120 V3 loop has been studied in the context of hybrid protein scaffolds or peptide fusions as a means of producing immunogens that could induce neutralizing antibodies against HIV-1. These materials could be important as components of an effective vaccine for combating the virus.

Monoclonal antibodies raised against synthetic V3 peptides which are known to react with gp120 were tested for binding to the recombinant UbV3 by ELISA. The antibody HG-1 specific for gp120 from the HIV-1 strain MN bound to UbV3 and to a 36-residue synthetic V3 loop "universal" peptide with similar efficiency. The binding to UbV3 was inhibited by preincubating the antibody with the 36-residue V3 peptide. Absorbance was reduced by 50% in the presence of 0.5 Fg/ml peptide. Antibody specific for gp120 of the IIIB strain did not bind UbV3.

Ubiquitin fusion proteins analyzed by SDS-PAGE were transferred to nitrocellulose membranes for Western blot assays. Strong staining was seen when membranes were developed with mAb HG-1 which is specific for the V3 sequence of gp120 from HIV-1 strain MN. No staining occurred with the mAb derived against the V3 peptide of gp120 of strain IIIB.

Immunogenicity of Ubiquitin and Ubiquitin Fusion Proteins

Immune responses in mice were evaluated from antiserum titers and from comparison at fixed dilutions of antisera taken at different times after immunizations. Reactivity against ubiquitin, UbV3 and UbgMT proteins, displaying either native ubiquitin epitopes alone, the "V3" epitope at the internal site or the MT sequence at the C-terminal site were assessed by ELISA with the proteins adsorbed to the solid support.

In the BALB/c (H-2d) strain a strong immune response was observed after an initial inoculation and one boost of either UbV3, UbV3aMT, or UbV3gMT fusion proteins. In contrast ubiquitin, given by an analogous protocol, was a poor immunogen (Table 1). Mice receiving two or more injections of ubiquitin over 4 weeks generally showed decreasing anti-ubiquitin reactive antibody. Mice immunized with fusion proteins UbV3, UbV3aMT and UbV3gMT produced antiserum specific for UbV3. The anti-UbV3 response continued to increase after an additional boost. Average titers of the final sera collected were in excess of 1:105. The antibody in these sera was shown to be primarily IgG. The V3 insert was the dominant B-cell target in all three immunogens. The sera bound only weakly or not at all to native ubiquitin or the UbMT fusion. Animals receiving UbgMT or UbaMT developed measurable antibody against UbgMT and ubiquitin. This response was directed partly to the C-terminal peptide as suggested by the higher ELISA signals obtained against the fusion protein compared with those against ubiquitin (Table 1).

TABLE 1

Summary of Immune Response Specificity to Antigens Displaying Heterologous and Native Ubiquitin Epitopes

| Strain: | BALB/c | Adjuvant: | CFA, or PN222/IFA |
|---|---|---|---|
| Routes: | SQ, IP | | |

| Immunogen[a] // Antigen[b] | Ub-V3 | Ub-MT | Ub |
|---|---|---|---|
| Ub-V3-rgg-MT | +++ | +/− | −− |
| Ub-V3-rga-MTc | +++ | +/− | −− |
| Ub-V3-rgg | ++ | −− | −− |
| Ub-rgg-MT | +/− | +++ | + |
| Ub-rga-MTc | −− | ++ | + |

(a) Fusion proteins were purified from E. coli lysates and purified by ion exchange chromatography. Solutions in Tris buffer, pH 7.4 were emulsified with Freund's complete adjuvant and injected as described.
(b) Antigens used to coat microtiter plates for ELISA were prepared from recombinant E. coli extracts and purified by ion exchange. Three antigens used displayed a single (V3 or MT) or no (Ub) heterologous epitope. Immunoreactivity is indicated by the relative scale from no reaction (−−) to strongest reaction (+++). Borderline reactivity (signal at the highest concentration of antisera used) is scored as +/−.
(c) Proteins with C-terminal fusions were produced with the native (rgg) and a mutated (rga) ubiquitin C-terminal sequence to test for stability to or assisted processing of the T-cell epitope by endogenous ubiquitin C-terminal hydrolases that may be present in antigen processing cells.

Immune Responses to Cleavable and Noncleavable C-terminal Fusions

Double epitope fusions had either the native ubiquitin C-terminus (UbV3gMT), retaining the processing site (RGG) for cleavage by cellular ubiquitin-specific proteases (UBPs), or a single residue mutation expressing the sequence RGA at the ubiquitin C-terminus (UbV3aMT), that is resistant to processing. Immunizations with the two types of double-epitope fusions were compared to determine if processing by UBPs in antigen presenting cells could influence a T-helper response. Since the antibody response to the V3 site was independent of the MT epitope in the BALB/c mouse, the effect of the processing mutation could not be observed in this strain. The immunogenicity in C57BL/6 (H-2b) and C3H (H-2k) mouse strains was determined after similar treatment. In both strains a specific anti-UbV3 or UbV3gMT. Responses against UbV3aMT were comparable in the two mouse strains when evaluated after two injections given two weeks apart. Immunoassays against ubiquitin and UbgMT, determined at 1/4000 serum dilution, indicated significantly lower antigenicity of these proteins. Signals were 16 and 35% of the values against UbV3 in the H-2b and H-2k mice, respectively. A second boost of the H-2b mice with double epitope fusion UbV3aMT produced improvements in the anti-UbV3 response similar to those seen in the BALB/c mice. The anti-UbV3 antiserum persisted at 3 weeks from the boost, although the signal at 1/4000 dilution was diminished by about 50% from sera collected in the previous bleed. Moreover, the anti-ubiquitin response was negligible in the mice that received the additional boosts. Immunizations with UbaMT produced antiserum of significant titer against all three antigens. A weaker, but similarly non-specific reaction was observed in mice inoculated with UbgMT. The anti-UbMT antisera reacted equivalently with native bovine ubiquitin and with recombinant ubiquitin but not with BSA. The anti-ubiquitin antibody persisted with additional immunizations.

Epitope Specificity of Antisera

Differences in antigenicity of the three proteins could suggest the epitope specificity of antisera for the V3 insert or the MT tag or specificity for discontinuous determinants composed of insert sequences as well as ubiquitin residues. Antiserum specific for UbV3 was incubated with short peptides analogous to the V3 sequence at varying concentrations, and residual unbound antibody measured by indirect ELISA. Reduction in signal was apparent in the 1-30 FM range of peptide concentration. By contrast, no competition was seen using ubiquitin at 10-100 FM as a competitor.

Anti-UbV3 sera reacted similarly with peptide L-V3 or a disulfide-bridged cyclic peptide C-V3 as mimics of the epitope. Although the peptide C-V3 could mimic the conformation of the V3 loop in the fusion protein this assay did not discriminate widely between the two peptides in solution.

Similar conformations of the V3 insert in the UbV3 and the V3 loop structure presented in gp120 could be suggested by better cross-reactivity of the antiserum with gp120. Adsorption of recombinant gp120 to ELISA plates appears to mask the V3 epitope such that detection of antibodies is inefficient. Binding to other epitopes on gp120 was detectable by direct or sandwich capture ELISA, but this technique was less successful with anti-V3 loop antibodies. Cross-reactivity of the anti-UbV3 antiserum for gp120 was demonstrated by Western blot analysis. Solution-phase competition binding as described for the V3 peptides using accessible concentrations of gp120 (#0.8 FM) did not produce measurable changes in the indirect ELISA.

T-Cell Proliferative Responses to Peptides and Ubiquitin Fusions

LN cells from BALB/c mice immunized with fusion proteins UbV3 or UbV3MT showed a proliferative response when cultured in the presence of UbV3 fusion. No obvious stimulation was provided by V3 or MT peptides at 100 Fg/ml, suggesting that the major T-helper epitope is not found in these sequences. No proliferation was observed in the presence of native bovine ubiquitin. In order to control for possible mitogenic contaminants contributed from the *E. coli* extracts, mice were immunized with recombinant ubiquitin or with buffer. LN cells from these mice were incubated in the presence of ubiquitin or UbV3. No proliferation was observed in any case. Potential T-helper epitopes in UbV3 could include sequences spanning the inserted residues and flanking ubiquitin sequences. Peptides representing these regions should be prepared and tested in the assay to address this point.

LN cells from C3H mice immunized with UbV3aMT were marginally stimulated by UbV3. However, incubation in the presence of increasing concentration of MT peptide, but not the V3 peptide, produced a significant proliferation signal. No stimulation was observed in the same experiment when C3H mice were immunized with UbV3. These preliminary experiments did not allow quantitation of the relative efficiency of T-cell stimulation by peptide and intact fusion proteins used as immunogen. Positive stimulation values were in the same range as those observed in the presence of concanavalin A added at 2-20 Fg/ml.

No. 2

Results

Production of Ubiquitin Fusion Proteins

Ubiquitin has been used as a scaffold for displaying multiple epitopes. These ubiquitin fusion proteins have been successfully recognized by antibodies of the appropriate specificity and analyzed using Origen technology. An immediate technological application for these ubiquitin fusion proteins that display a structurally defined antigenic epitope which is known to be a target for neutralizing antibodies is in production of diagnostic antibodies for clinical or research use. The advantages conferred by the use of ubiquitin as a scaffold include: 1) its ability to stabilize the epitopes in storage, and in in vitro assays, and 2) its ability to constrain the peptide at one or both ends, thereby conferring the appropriate conformation for antibody recognition.

A commonly used sandwich immunoassay requires two distinct monoclonal antibodies against a single macromolecular analyte, in the present case the ubiquitin fusion proteins. These antibodies are directed to nonoverlapping epitopes on the ubiquitin fusion proteins, allowing the formation of a trimeric complex, or sandwich. Typically, many monoclonal antibodies must be screened in order to identify an appropriate pair for the immunoassay. The technology described here permits the production of monoclonal or polyclonal antibodies against structurally defined epitopes in a macromolecule. Thus, a pair of reagent antibodies for a sandwich immunoassay may be produced by design rather than by random screening. Such reagents may be employed in a wide variety of important immunoassays utilizing any number of formats that are standard in the industry.

Construction of Ubiquitin Fusion Proteins

In Example 2, several ubiquitin fusions were constructed. These ubiquitin fusions contain a peptide epitope loop derived from the human PSA (prostate specific antigen). As shown in Table 2 below, ubiquitin fusion proteins contained either single or double epitope insertions on the ubiquitin scaffold. Four different versions of an antigenic PSA peptide loop from human prostate specific antigen were inserted into the ubiquitin scaffold at amino acid position 35. In Table 2 below they are labeled as Fus 5, Fus 5M, Fus 7 and Fus 7M. Four C-terminal fusions were also constructed, both individually and in various combinations with the fusions inserted into the ubiquitin scaffold at amino acid position 35. The peptides joined to the C-terminus of the ubiquitin fusions are shown below in Table 2. They include ATNAT, FLAG, PSA conpep and Fus 7 conpep. The "PSA conpep" fusions contain a modification at amino acid 76 of the ubiquitin to prevent cleavage by a ubiquitin specific protease. These fusions were produced for testing by growth and isolation from bacterial cultures transformed with DNA constructs that encode the ubiquitin fusion proteins. The bacterial lysate from these transformed cultures is nearly homogeneous with respect to protein content. Thus, dilution was sufficient for the following experimentation.

TABLE 2

Single and Double Insertions on the Ubipuitin Scaffold

| | | | | |
|---|---|---|---|---|
| Fus 5 | 92 AA | 10.44 k | pI 8.20 | KE-DVCAQVHPQKVTKFMLC-IPP (SEQ ID NO: 18) |
| Fus 5 M | 90 AA | 10.24 k | pI 8.63 | KE-DVCAQVHPQKVTKFMLC-MPP (SEQ ID NO: 19) |
| Fus 7 | 90 AA | 10.22 k | pI 8.81 | KE-CAQVHPQKVTKFMLC-IPP (SEQ ID NO: 20) |
| Fus 7 M | 87 AA | 98.93 k | pI 9.26 | KE-CAQVHPQKVTKFM-PP (SEQ ID NO: 21) |
| ATNAT | 104 AA | 11.63 k | pI 9.65 | RGG-SLRRSSCFGGRMDRI GAQSGLGCNSFRY (SEQ ID NO: 22) |
| FLAG | 98 AA | 11.22 k | pI 6.12 | RGG-DYKDD DDK (SEQ ID NO: 23) |
| PSA conpep (W/O FUS 7) | 96 AA | 10.99 k | pI 9.71 | RGA-LYTKVVHYRKWIKDTIVANP(SEQ ID NO: 24) |
| Fus 7 conpep | 110 AA | 12.65 k | pI 9.67 | RGA-LYTKVVHYRKWIKDTIVANP(SEQ ID NO: 24) |

Competition Analysis of Single Epitope Ubiquitin

The polyclonal antibody raised to a KLH conjugated peptide bound to the PSA peptide in the ubiquitin fusion. This PSA ubiquitin fusion was able to act like the native PSA by competing with native PSA for binding to this polyclonal antibody in an elisa assay.

In vivo Cleavage of Double Epitope Ubiquitin Fusions

The structural authenticity of the ubiquitin scaffold in maintaining the secondary structure of the PSA peptide inserted internally at position 35 was probed by an in vivo assay. The assay involved the cleavage of the C-terminal PSA peptide from the double epitope ubiquitin fusion protein by a ubiquitin specific protease. Bacteria were transformed with DNA expression constructs for a double epitope ubiquitin fusion protein, UbFus7-conpep or UbFus7-ATNAT shown above in Table 2 and a ubiquitin containing plasmid. SDS-PAGE analysis of whole bacterial cell lysates showed that the UBFus7-ATNAT ubiquitin double epitope fusion protein was cleaved in vivo, liberating the C-terminal peptide from the main body of the ubiquitin fusion protein. Following the successful cleavage of the double epitope fusion UbFus7-ATNAT by in vivo ubiquitin specific proteases, the portion of the ubiquitin fusion protein which contained the internal insertion was analyzed. Based on this cleavage activity, it was deduced that a ubiquitin fusion protein with an internal insert would maintain its basic structure despite the 15 amino acid insertion of the PSA peptide at position 35. On the other hand, UbFus7-conpep fusion protein, which was modified at the C-terminus to prevent cleavage by a ubiquitin specific protease remained intact. No ubiquitin specific protease cleavage fragments were identified with UbFus7-conpep, as expected.

Direct Binding of Double Epitope Ubiquitin Fusion

The proof of concept that a double epitope ubiquitin fusion could be utilized in a sandwich assay was shown by two different direct-binding immunoassays using methods known to those skilled in the art. In one of these immunoassays, the quantity of the double epitope ubiquitin fusion protein UbFus7-Flag used in the immunoassay was kept constant, while the concentration of the anti-PSA specific polyclonal serum was diluted out from 1×10-2 to 1×10-5. The intensity of signal for the anti-PSA specific polyclonal serum for the ubiquitin fusion protein as measured by ECL (IGEN, Inc.) decreased in a linear manner as the quantity of antibody was diluted out. A similar result was found in a second direct-binding immunoassay. In this assay, the double epitope ubiquitin fusion protein was titered out from 10,000 ng/ml UbFus7-Flag to 0.1 ng/ml UbFus7-Flag, while the quantity of anti-PSA polyclonal serum was kept constant. As seen for the first experimental assay, the intensity of signal for the anti-PSA polyclonal serum as measured by ECL intensity decreased in a linear manner as the quantity of UbFus7-Flag was reduced. Thus, the anti-PSA polyclonal serum antibody showed a high degree of binding specificity for the double epitope ubiquitin fusions. This dual recognition supports the notion that the double epitope ubiquitin fusions can serve as calibrators in a sandwich immunoassay.

No. 3

Results

Ubiquitin GnRH Immunogens

In order to generate an ubiquitin fusion protein which is able to stimulate the production of self antibodies, a fusion protein was constructed which contained a C-terminal extension to ubiquitin with the following sequence of the GnRH dimer; QHWSYGLRPGQHWSYGLRPG (SEQ ID NO:26) followed by a T cell epitope, DDPKTGQFLQQINA-YARPSEV (corona virus T cell epitope) (SEQ ID NO:27) or DQVHFQPLPPAVVKLSDAL (MT epitope) (SEQ ID NO:17). This was constructed using standard methods known to one of skill in the art with sets of synthetic oligonucleotides. The ubiquitin used in these constructs was also modified so that its last amino acid was replaced by a valine to render the fusions noncleavable by ubiquitin-specific proteases. These ubiquitin fusions were expressed as described in Example 1 above and purified by ion exchange chromatography and HPLC (when necessary) following standard protocols. The ubiquitin fusion protein were purified to greater than 90% purity.

The purified ubiquitin fusion proteins were then formulated with adjuvants as described in Example 1 above and used to immunize mice. The mice were re-immunized about 25-30 days following the initial immunization. Sera prepared following bleeds from the mice were tested to determine the level of epitope specific antibodies which were induced by the specific ubiquitin fusion proteins. The results demonstrated that the immunizations resulted in the induction of high levels of anti-GnRH antibodies.

Other immunogens which were constructed include ubiquitin with an internal GnRH epitope as a single and as a double epitope at position 35 of ubiquitin and T cell epitopes attached at the C-terminus as described above. To further increase the epitope density, the ubiquitin fusion protein with the internal GnRH dimer at position 35 is also fused at its C-terminus with a dimer of GnRH followed by a T cell epitope or with MT at the C-terminus followed by GnRH.

In further variations of the ubiquitin fusion protein design which have been described above, the T cell epitope was attached at the C-terminus of ubiquitin which is then fused to the dimer or monomer sequence of GnRH.

The GnRH monomer can consist of EHWSYGLRPG (SEQ ID NO:28) with a corresponding dimer of EHWSYGL-RPGEHWSYGLRPG (SEQ ID NO:29) or a mixed dimer of EHWSYGLRPGQHWSYGLRPG (SEQ ID NO:30) or QHWSYGLRPGEHWSYGLRPG (SEQ ID NO:31). Alter-

No. 4

N-Terminal Fusions of GnRH to Ubiquitin for Immunocastration

Novel constructs are prepared by placing an epitope at the N-terminus of a first ubiquitin protein to create a fusion protein which can elicit a desired immune response. These constructs differ from those in the prior art by allowing placement of any epitope at the N-terminus of the first ubiquitin protein in order to produce an effective vaccine conjugate.

One use for this type of novel N-terminal epitope presentation is in the generation of an anti-self antibody response. Expression vectors capable of this include those generated for immunocastration. These vectors are based on the vaccine constructs described above in Example 3. However, in the present example, the vaccine constructs include a N terminal ubiquitin protein fused to the N-terminus of the epitope attached to the N-terminus of the C terminal ubiquitin protein. Linkage of the N terminal ubiquitin protein to the N-terminal epitope is through a ubiquitin specific cleavable C-terminus. For example, in the case of GnRH, the sequence coding for (QHWSYGLRPG)n (SEQ ID NO:32), where n is from 1-8, is fused to the 3' end of the second ubiquitin protein using synthetic oligonucleotides and methods known to one of skill in the art. The resultant gene sequence contains a fusion protein comprised of an epitope flanked on its C-terminus by a C terminal ubiquitin protein and on its N-terminus by a N terminal ubiquitin protein. The ubiquitin proteins joined to GnRH can be used to generate a number of possible combinations of fusion proteins containing multiple GnRH sequences and T cell epitopes.

The fusion between the N terminal ubiquitin protein and an N-terminal epitope can occur via an RGG native ubiquitin C-terminus and a Q at the N-terminus of the GnRH sequence. In this example, the GnRH epitope sequence is comprised of from 1 to 8 copies of the following sequence QHWSYGL-RPG (SEQ ID NO:32). The fusion protein comprising the GnRH epitope flanked on both its N- and C-terminal ends may be fused to at least one T cell epitope such as DQVH-FQPLPPAVVKLSDAL (SEQ ID NO:17) at its C-terminus via a non-native ubiquitin C-terminal sequence such as RGV to render it non-cleavable by the ubiquitin specific proteases. Variations on the basic construct described above are made using different C terminal ubiquitin fusion proteins. Examples of these can be found in Example 3 above. For instance, the C terminal ubiquitin protein can be further modified to include GnRH epitopes (from 1 to 8 epitopes) inserted at position 35. In addition, the T cell epitope(s) fused to the C-terminus of the C terminal ubiquitin protein can be varied.

To prepare the N-terminal epitope ubiquitin fusion proteins, these gene constructs are placed within the expression vector described in Example 1 and used to transform *E. coli* for protein expression. The expressed protein is isolated from the *E. coli* cells by sonication followed by ion exchange purification to give a preparation which can then be subjected to the action of a ubiquitin specific protease (UBP). Digestion of the fusion protein with the UBP results in the release of the N-terminal ubiquitin protein from the N-terminus of the N-terminally fused epitope. This cleavage reaction is then subjected to a further ion exchange purification to yield a fusion protein with a GnRH epitope(s) fused to the N-terminus of the COOH terminal ubiquitin protein. The purified ubiquitin fusion protein, with its N-terminal and or C-terminal epitopes, can now be formulated to generate the vaccine for study as described in Example 6.

No. 5

Conjugation of Ubiquitin GnRH Fusion Proteins to Carrier Proteins

Ubiquitin fusion proteins containing peptide epitopes can be efficiently coupled directly to another protein. In the present example, two ubiquitin-GnRH fusion proteins are created which are site specifically coupled to ovalbumin. These ubiquitin-GnRH fusion proteins are constructed using synthetic oligonucleotides, which encode the GnRH sequence; QHWSYGLRPGQHWSYGLRPGQHWSYGLR-PGQHWSYGLRPGC (SEQ ID NO:34) for one construct and QHWSYGLRPGQHWSYGLRPGQHWSYGLR-PGQHWSYGLRPG (SEQ ID NO:35) for the second construct.

These oligonucleotides are cloned into the UBP-cleavable C-terminal site in the coding sequence of ubiquitin as described above in Example 1. The resulting fusion constructs consist of the coding sequence for ubiquitin fused to four copies of the GnRH epitope, with both containing either a C-terminal Cys or not. To regulate expression, the coding sequence was placed under the control of a lac promoter which when induced elicits high levels of expressed fusion protein. The resulting construct is used to transform *E. coli* as described above in Example 1 and the cells were cultured followed by induction of expression of the fusion protein. The fusion protein was isolated from the *E. coli* cell pellet by first subjecting the cells to sonication, followed by purification of the fusion protein by ion exchange chromatography.

Conjugation of Ubiquitin Fusions with the C Terminal Cys

Ovalbumin is activated by reaction with N-succinimidyl-3-(2-pyridyldithio)-propionate (SPDP) or by succinimidyl 4-(N-maleimido-methyl) cyclohexane-1-carboxylate (SMCC) followed by gel filtration to remove unreacted cross linking agents. Ubiquitin fusion protein is coupled to ovalbumin by reacting it with activated ovalbumin. The resultant reaction between a free SH group present on the ubiquitin fusion protein and the activated ovalbumin results in a covalent linkage through either a thiol ether linkage with the SMCC activated ovalbumin or a disulfide bond from the reaction with the SPDP activated ovalbumin. The resultant conjugate is formulated with an adjuvant such as Quil-A, complete Freunds adjuvant (CFA) or incomplete Freunds adjuvant (IFA) and then used for immunization as described in Example 6 below.

Conjugation of Ubiquitin Fusions without the C Terminal Cys

The ubiquitin fusion protein is coupled to ovalbumin by reacting it with ovalbumin in the presence of a cross linking agent such as disuccinimidyl suberate or gluteraldehyde (Pierce). The resultant reaction the ubiquitin fusion protein and ovalbumin results in a covalent linkage through amino groups on the ubiquitin fusion protein and ovalbumin. The resultant conjugate is formulated with an adjuvant such as Quil-A, complete Freunds adjuvant (CFA) or incomplete Freunds adjuvant (IFA) and then used for immunization as described in Example 6 below.

No. 6

Immunocastration of Pigs with Ubiquitin GnRH Immunogens

The ubiquitin fusion protein immunogens constructed as described above in Examples 3, 4 and 5 were tested in piglets. Male piglets which were between the age of 9-10 weeks were immunized with 1-10 mg of the ubiquitin GnRH immunogens in complete Freund's adjuvant (CFA) intramuscularly. Immunizations were repeated 8 weeks following the initial CFA immunization, with IFA. The piglets were slaughtered 16 weeks after the initial immunization at which time the testicles were excised and weighed. In addition, the serum testosterone levels of the piglets was determined along with the androstenone levels in fat. All the animals immunized with the ubiquitin GnRH immunogens showed significant reduction in testicular weight, along with significantly reduced levels of testosterone in the serum. The levels of androstenone in fat were below 0.1 Fg/ml. These experiments have demonstrated the potential of the ubiquitin fusion proteins to act as an immunogen for the generation of self immune responses known more specifically as immunocastration.

No. 7

Growth Hormone Vaccine to Enhance the Growth Rate

In order to improve the growth rate of pigs, a vaccine was constructed which included the insertion of a growth hormone epitope into ubiquitin. Prior studies have shown that the epitope encoded by amino acids 54-95 of growth hormone can be used to make a vaccine which improves the growth rate of pigs by increasing the activity of the endogenous growth hormone. By using ubiquitin fusion proteins containing this growth hormone epitope, novel vaccines can be generated which offer the advantages of enhanced hormone activity and lower costs.

In the present example, the growth hormone epitope was inserted into ubiquitin as described in Examples 3, 4 and 5 above, with the growth hormone epitope inserted at the same sites described above for the GnRH epitopes. The growth hormone epitope can be inserted as a multimer, with up to four contiguous repeats to enhance its immunogenicity. Constructs encoding the growth hormone-ubiquitin fusion proteins were transformed into and expressed in $E.$ $coli$, followed by purification of the fusion protein by methods described above.

The purified growth hormone-ubiquitin fusion proteins were formulated with adjuvant and used to immunize pigs weighing 15-20 kg. CFA was used for the first immunization followed by two subsequent booster injections with IFA. These subsequent booster injections were each given at 4 week intervals following the initial injection. Pigs were monitored until they reached a weight of 110-120 Kg at which time the animals were killed. The resultant weight gain by immunized pigs when compared to control animals receiving only adjuvant or ubiquitin only and adjuvant demonstrated the improved growth rates of the immunized pigs.

---

The invention claimed is:

1. A method for detecting the presence of specific antibodies in experimental or clinical samples, comprising:
   a) providing a ubiquitin fusion protein selected from the group consisting of i) a ubiquitin fusion protein comprising ubiquitin fused to a single epitope-containing segment, the epitope-containing segment comprising two or more identical epitopes, ii) a ubiquitin fusion protein comprising ubiquitin fused to two or more non-contiguous epitope-containing segments, each epitope-containing segment comprising one or more identical epitopes, iii) a ubiquitin fusion protein comprising ubiquitin fused to a single epitope-containing segment comprising two or more identical epitopes, the epitope-containing segment being fused to the ubiquitin at fusion sites selected from the group consisting of the C-terminus of the ubiquitin protein wherein said fusion site is non-cleavable, the N-terminus of the ubiquitin protein or an internal fusion site of the ubiquitin protein and, iv) a ubiquitin fusion protein comprising ubiquitin fused to a single epitope-containing segment comprising two or more identical epitopes, the epitope-containing segment being fused to ubiquitin at the C-terminus wherein said fusion site is non-cleavable or the N-terminus of the ubiquitin protein, wherein one or more epitopes of steps (a)(i)-(a)(iv) are recognized by the antibody to be detected;
   b) providing a sample suspected of comprising antibodies reactive with one or more epitopes of the ubiquitin fusion protein, said sample acquired from an experimental or clinical source;
   c) forming an incubation mixture comprising the ubiquitin fusion protein of step a) and the sample of step b); and
   d) detecting antibodies in the sample of step b) that bind to the epitope or epitopes of the ubiquitin fusion protein of step a) and wherein said epitopes of step a) are selected from the group consisting of HIV gp 120 V3 loop epitopes, GnRH epitopes and Growth Hormone epitopes.

2. The method of claim 1, wherein said epitopes are HIV gp 120 V3 loop epitopes.

3. The method of claim 1, wherein said epitopes are GnRH epitopes.

4. The method of claim 1, wherein said epitopes are Growth Hormone epitopes.

* * * * *

UNITED STATES PATENT AND TRADEMARK OFFICE
CERTIFICATE OF CORRECTION

PATENT NO. : 7,662,642 B2  
APPLICATION NO. : 10/681388  
DATED : February 16, 2010  
INVENTOR(S) : Kenten et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 98 days.

Signed and Sealed this

Thirtieth Day of November, 2010

David J. Kappos  
*Director of the United States Patent and Trademark Office*

SEQUENCE LISTING

```
<160> NUMBER OF SEQ ID NOS: 35

<210> SEQ ID NO 1
<211> LENGTH: 35
<212> TYPE: PRT
<213> ORGANISM: Artificial Sequence
<220> FEATURE:
<223> OTHER INFORMATION: Description of Artificial Sequence: cloning
      oligo

<400> SEQUENCE: 1

Cys Thr Arg Pro Asn Asn Asn Thr Arg Lys Ser Ile His Ile Gly Pro
 1               5                  10                  15

Gly Arg Ala Phe Tyr Thr Thr Gly Glu Ile Ile Gly Asp Ile Arg Gln
            20                  25                  30

Ala His Cys
        35

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: cloning
      oligo

<400> SEQUENCE: 2

Lys Arg Ile His Ile Gly Pro Gly Arg Ala Phe Tyr Thr Thr Lys
 1               5                  10                  15

<210> SEQ ID NO 3
<211> LENGTH: 17
```

```
<212> TYPE: PRT
<213> ORGANISM: Artificial Sequence
<220> FEATURE:
<223> OTHER INFORMATION: Description of Artificial Sequence: cloning
      oligo

<400> SEQUENCE: 3

Cys Lys Ser Ile His Ile Gly Pro Gly Arg Ala Phe Tyr Thr Thr Gly
 1               5                  10                  15
Cys

<210> SEQ ID NO 4
<211> LENGTH: 50
<212> TYPE: DNA
<213> ORGANISM: Artificial Sequence
<220> FEATURE:
<223> OTHER INFORMATION: Description of Artificial Sequence: cloning
      oligo

<400> SEQUENCE: 4
ttaagactgc gtggcggcga ccaggttcac ttccagccgc tgccgccggc            50

<210> SEQ ID NO 5
<211> LENGTH: 37
<212> TYPE: DNA
<213> ORGANISM: Artificial Sequence
<220> FEATURE:
<223> OTHER INFORMATION: Description of Artificial Sequence: cloning
      oligo

<400> SEQUENCE: 5
tgttgttaaa ctgtctgacg ctctgtaagc ttctgca                         37

<210> SEQ ID NO 6
<211> LENGTH: 43
<212> TYPE: DNA
<213> ORGANISM: Artificial Sequence
<220> FEATURE:
<223> OTHER INFORMATION: Description of Artificial Sequence: cloning
      oligo

<400> SEQUENCE: 6
gaagcttaca gagcgtcaga cagtttaaca acagccggcg gca                  43

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: cloning
      oligo

<400> SEQUENCE: 7
gcggctggaa gtgaacctgg tcgccgccac gcagtc                          36

<210> SEQ ID NO 8
<211> LENGTH: 50
<212> TYPE: DNA
<213> ORGANISM: Artificial Sequence
<220> FEATURE:
<223> OTHER INFORMATION: Description of Artificial Sequence: cloning
      oligo

<400> SEQUENCE: 8
ttaagactgc gtggcgctga ccaggttcac ttccagccgc tgccgccggc            50
```

```
<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: cloning
      oligo

<400> SEQUENCE: 9
gcggctggaa gtgaacctgg tcagcgccac gcagtc                                 36

<210> SEQ ID NO 10
<211> LENGTH: 55
<212> TYPE: DNA
<213> ORGANISM: Artificial Sequence
<220> FEATURE:
<223> OTHER INFORMATION: Description of Artificial Sequence: cloning
      oligo

<400> SEQUENCE: 10
aagaaatcca catcggtccg ggtcgtgctt tctacaccac catcccgccg gatca            55

<210> SEQ ID NO 11
<211> LENGTH: 54
<212> TYPE: DNA
<213> ORGANISM: Artificial Sequence
<220> FEATURE:
<223> OTHER INFORMATION: Description of Artificial Sequence: cloning
      oligo

<400> SEQUENCE: 11
atccggcggg atggtggtgt agaaagcacg acccggaccg atgtggattt cttt             54

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: cloning
      oligo

<400> SEQUENCE: 12
ttaagactgc gtggcggcat ccacatcggt ccg                                    33

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: cloning
      oligo

<400> SEQUENCE: 13
ggtcgtgctt tctacaccac ctaactgca                                         29

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence: cloning
      oligo

<400> SEQUENCE: 14
gttaggtggt gtagaaagca cgacccggac cgat                                   34

<210> SEQ ID NO 15
```

```
<211> LENGTH: 20
<212> TYPE: DNA
<213> ORGANISM: Artificial Sequence
<220> FEATURE:
<223> OTHER INFORMATION: Description of Artificial Sequence: cloning
      oligo

<400> SEQUENCE: 15
gtggatgccg ccacgcagtc                                              20

<210> SEQ ID NO 16
<211> LENGTH: 12
<212> TYPE: PRT
<213> ORGANISM: HIV-1

<400> SEQUENCE: 16

Ile His Ile Gly Pro Gly Arg Ala Phe Tyr Thr Thr
  1               5                  10

<210> SEQ ID NO 17
<211> LENGTH: 19
<212> TYPE: PRT
<213> ORGANISM: Mycobacterium tuberculosis

<400> SEQUENCE: 17

Asp Gln Val His Phe Gln Pro Leu Pro Pro Ala Val Val Lys Leu Ser
  1               5                  10                  15

Asp Ala Leu

<210> SEQ ID NO 18
<211> LENGTH: 22
<212> TYPE: PRT
<213> ORGANISM: Homo sapiens

<400> SEQUENCE: 18

Lys Glu Asp Val Cys Ala Gln Val His Pro Gln Lys Val Thr Lys Phe
  1               5                  10                  15

Met Leu Cys Ile Pro Pro
             20

<210> SEQ ID NO 19
<211> LENGTH: 22
<212> TYPE: PRT
<213> ORGANISM: Homo sapiens

<400> SEQUENCE: 19

Lys Glu Asp Val Cys Ala Gln Val His Pro Gln Lys Val Thr Lys Phe
  1               5                  10                  15

Met Leu Cys Met Pro Pro
             20

<210> SEQ ID NO 20
<211> LENGTH: 20
<212> TYPE: PRT
<213> ORGANISM: Homo sapiens

<400> SEQUENCE: 20

Lys Glu Cys Ala Gln Val His Pro Gln Lys Val Thr Lys Phe Met Leu
  1               5                  10                  15

Cys Ile Pro Pro
         20

<210> SEQ ID NO 21
```

```
<211> LENGTH: 17
<212> TYPE: PRT
<213> ORGANISM: Homo sapiens

<400> SEQUENCE: 21

Lys Glu Cys Ala Gln Val His Pro Gln Lys Val Thr Lys Phe Met Pro
 1               5                  10                  15
Pro

<210> SEQ ID NO 22
<211> LENGTH: 31
<212> TYPE: PRT
<213> ORGANISM: Homo sapiens

<400> SEQUENCE: 22

Arg Gly Gly Ser Leu Arg Arg Ser Ser Cys Phe Gly Gly Arg Met Asp
 1               5                  10                  15

Arg Ile Gly Ala Gln Ser Gly Leu Gly Cys Asn Ser Phe Arg Tyr
            20                  25                  30

<210> SEQ ID NO 23
<211> LENGTH: 11
<212> TYPE: PRT
<213> ORGANISM: Homo sapiens

<400> SEQUENCE: 23

Arg Gly Gly Asp Tyr Lys Asp Asp Asp Asp Lys
 1               5                  10

<210> SEQ ID NO 24
<211> LENGTH: 23
<212> TYPE: PRT
<213> ORGANISM: Homo sapiens

<400> SEQUENCE: 24

Arg Gly Ala Leu Tyr Thr Lys Val Val His Tyr Arg Lys Trp Ile Lys
 1               5                  10                  15

Asp Thr Ile Val Ala Asn Pro
            20

<210> SEQ ID NO 25
<211> LENGTH:
<212> TYPE:
<213> ORGANISM:

<400> SEQUENCE: 25

000

<210> SEQ ID NO 26
<211> LENGTH: 20
<212> TYPE: PRT
<213> ORGANISM: Porcine

<400> SEQUENCE: 26

Gln His Trp Ser Tyr Gly Leu Arg Pro Gly Gln His Trp Ser Tyr Gly
 1               5                  10                  15

Leu Arg Pro Gly
            20

<210> SEQ ID NO 27
<211> LENGTH: 21
<212> TYPE: PRT
<213> ORGANISM: cor

-continued

```
<400> SEQUENCE: 27

Asp Asp Pro Lys Thr Gly Gln Phe Leu Gln Gln Ile Asn Ala Tyr Ala
1               5                   10                  15

Arg Pro Ser Glu Val
            20

<210> SEQ ID NO 28
<211> LENGTH: 10
<212> TYPE: PRT
<213> ORGANISM: Porcine

<400> SEQUENCE: 28

Glu His Trp Ser Tyr Gly Leu Arg Pro Gly
1               5                   10

<210> SEQ ID NO 29
<211> LENGTH: 20
<212> TYPE: PRT
<213> ORGANISM: Porcine

<400> SEQUENCE: 29

Glu His Trp Ser Tyr Gly Leu Arg Pro Gly Glu His Trp Ser Tyr Gly
1               5                   10                  15

Leu Arg Pro Gly
            20

<210> SEQ ID NO 30
<211> LENGTH: 20
<212> TYPE: PRT
<213> ORGANISM: Porcine

<400> SEQUENCE: 30

Glu His Trp Ser Tyr Gly Leu Arg Pro Gly Gln His Trp Ser Tyr Gly
1               5                   10                  15

Leu Arg Pro Gly
            20

<210> SEQ ID NO 31
<211> LENGTH: 20
<212> TYPE: PRT
<213> ORGANISM: Porcine

<400> SEQUENCE: 31

Gln His Trp Ser Tyr Gly Leu Arg Pro Gly Glu His Trp Ser Tyr Gly
1               5                   10                  15

Leu Arg Pro Gly
            20

<210> SEQ ID NO 32
<211> LENGTH: 10
<212> TYPE: PRT
<213> ORGANISM: Porcine

<400> SEQUENCE: 32

Gln His Trp Ser Tyr Gly Leu Arg Pro Gly
1               5                   10

<210> SEQ ID NO 33
<211> LENGTH:
<212> TYPE:
<213> ORGANISM:
```

```
<400> SEQUENCE: 33

000

<210> SEQ ID NO 34
<211> LENGTH: 41
<212> TYPE: PRT
<213> ORGANISM: Porcine

<400> SEQUENCE: 34

Gln His Trp Ser Tyr Gly Leu Arg Pro Gly Gln His Trp Ser Tyr Gly
  1               5                  10                  15

Leu Arg Pro Gly Gln His Trp Ser Tyr Gly Leu Arg Pro Gly Gln His
             20                  25                  30

Trp Ser Tyr Gly Leu Arg Pro Gly Cys
         35                  40

<210> SEQ ID NO 35
<211> LENGTH: 40
<212> TYPE: PRT
<213> ORGANISM: Porcine

<400> SEQUENCE: 35

Gln His Trp Ser Tyr Gly Leu Arg Pro Gly Gln His Trp Ser Tyr Gly
  1               5                  10                  15

Leu Arg Pro Gly Gln His Trp Ser Tyr Gly Leu Arg Pro Gly Gln His
             20                  25                  30

Trp Ser Tyr Gly Leu Arg Pro Gly
         35                  40
```